(12) United States Patent
Purdy et al.

(10) Patent No.: US 12,043,820 B2
(45) Date of Patent: Jul. 23, 2024

(54) HARD SURFACE CLEANING COMPOSITION

(71) Applicant: Fluid Energy Group Ltd., Calgary (CA)

(72) Inventors: Clay Purdy, Medicine Hat (CA); Markus Weissenberger, Calgary (CA); Kyle G. Wynnyk, Calgary (CA); Karl W. Dawson, Calgary (CA)

(73) Assignee: FLUID ENERGY GROUP LTD., Calgary (CA)

( * ) Notice: Subject to any disclaimer, the term of this patent is extended or adjusted under 35 U.S.C. 154(b) by 125 days.

(21) Appl. No.: 17/705,142

(22) Filed: Mar. 25, 2022

(65) Prior Publication Data
US 2022/0315863 A1 Oct. 6, 2022

(30) Foreign Application Priority Data
Mar. 30, 2021 (CA) .................................. 3113508

(51) Int. Cl.
| | | |
|---|---|---|
| *C11D 3/33* | (2006.01) | |
| *A61L 2/18* | (2006.01) | |
| *C11D 1/12* | (2006.01) | |
| *C11D 1/22* | (2006.01) | |
| *C11D 1/28* | (2006.01) | |
| *C11D 3/30* | (2006.01) | |
| *C11D 3/32* | (2006.01) | |
| *C11D 3/34* | (2006.01) | |
| *C11D 3/39* | (2006.01) | |
| *C11D 3/395* | (2006.01) | |
| *C11D 3/48* | (2006.01) | |
| *C11D 7/32* | (2006.01) | |
| *C11D 7/34* | (2006.01) | |
| *A61L 101/02* | (2006.01) | |

(52) U.S. Cl.
CPC ................ *C11D 1/22* (2013.01); *A61L 2/186* (2013.01); *C11D 1/12* (2013.01); *C11D 1/28* (2013.01); *C11D 3/30* (2013.01); *C11D 3/32* (2013.01); *C11D 3/34* (2013.01); *C11D 3/3418* (2013.01); *C11D 3/3902* (2013.01); *C11D 3/394* (2013.01); *C11D 3/3942* (2013.01); *C11D 3/48* (2013.01); *C11D 7/3209* (2013.01); *C11D 7/3263* (2013.01); *C11D 7/34* (2013.01); *A61L 2101/02* (2020.08); *C11D 2111/14* (2024.01)

(58) Field of Classification Search
CPC .... C11D 1/12; C11D 1/28; C11D 3/30; C11D 3/32; C11D 3/34; C11D 3/3418; C11D 3/3902; C11D 7/3209; C11D 7/3263; C11D 7/34
USPC ................ 510/238, 372, 426, 495, 499, 501
See application file for complete search history.

(56) References Cited

U.S. PATENT DOCUMENTS

| | | | |
|---|---|---|---|
| 4,690,779 A | 9/1987 | Baker et al. | |
| 5,011,538 A * | 4/1991 | Smith .................. | C11D 3/3956 134/22.13 |
| 5,252,245 A | 10/1993 | Garabedian, Jr. et al. | |
| 5,437,807 A | 8/1995 | Garabedian, Jr. et al. | |
| 5,468,423 A | 11/1995 | Garabedian, Jr. et al. | |
| 5,585,342 A | 12/1996 | Choy et al. | |
| 2011/0230385 A1* | 9/2011 | Murphy ............... | C11D 3/2086 510/382 |
| 2014/0121147 A1* | 5/2014 | Tajmamet ............ | C11D 3/2086 510/235 |

FOREIGN PATENT DOCUMENTS

| | | | | |
|---|---|---|---|---|
| EP | 0393772 A2 | 10/1990 | | |
| EP | 0428816 A1 | 5/1991 | | |
| EP | 962520 A1 * | 12/1999 | ............... | C11D 1/94 |
| EP | 2216392 A1 * | 8/2010 | ............. | C11D 3/227 |
| GB | 2160887 A | 1/1986 | | |
| WO | WO-2005113735 A1 * | 12/2005 | ............. | C11D 1/835 |

\* cited by examiner

*Primary Examiner* — Gregory R Delcotto
(74) *Attorney, Agent, or Firm* — Berg Hill Greenleaf Ruscitti LLP

(57) ABSTRACT

A composition for use as a hard surface cleaner, sanitizer and/or disinfectant is disclosed. The composition according to one embodiment comprises an arylsulfonic acid, a source of peroxide, an effective amount of a stabilizer and water. A method is provided of cleaning, disinfecting and/or sanitizing a hard surface, the method comprising providing the composition, providing a surface which requires cleaning and applying the composition onto the surface for a duration of time sufficiently long enough to destroy micro-organisms present on the surface.

16 Claims, No Drawings

HARD SURFACE CLEANING COMPOSITION

CROSS REFERENCE TO RELATED APPLICATIONS

This application claims the benefit of and priority to Canadian Patent Application No. 3,113,508, filed Mar. 30, 2021. The entire specification and figures of the above-referenced application are hereby incorporated, in their entirety by reference.

FIELD OF THE INVENTION

The invention is for a hard surface cleaning, sanitizing and/or disinfecting composition specifically adapted for use on non-porous hard surfaces, more specifically, to aqueous acidic compositions used as a hard surface cleaner, sanitizer and/or disinfectant.

BACKGROUND OF THE INVENTION

Microorganisms such as bacteria, fungi, viruses, or algae are present in every single environment inhabited by humans. While microorganisms are frequently an essential part of ecological systems; industrial processes; and human bodily functions, such as digestion, some microorganisms are highly undesirable. They may be the source of widespread illness, disease and even death for animals as well as humans.

In times of pandemics, there is an increased need for cleaning, sanitizing, and/or disinfecting for domestic and industrial settings as establishments, health care facilities and food supply chains. To prevent the spread of microorganisms, viruses, and pathogens, surfaces must be cleaned, sanitized and/or disinfected. The type and prevalence of microorganisms present depends on a number of factors, among which are: the availability of nutrients and moisture; humidity levels; temperature; human exposure levels, and surface roughness. Certain microorganism bacteria are capable of remaining viable in a dormant state on floors, tables, cabinets, handles or on other objects for extended periods of time until they are deposited or transferred to the proper media for growth.

Nutrients for microorganisms are typically abundant. For example, dried skin, discarded food, plants, animal wastes, synthetic and natural materials like: plastic coatings and objects, wood, paper, and natural fibers are all excellent nutrient media for many types of microorganisms, including potentially damaging organisms.

A major challenge within the health care field and now public and private spaces in general, is the prevention of the spread of dangerous infectious diseases by microorganisms and the associated human transmission. Facilities such as hospitals, office spaces, restaurants, gyms, nightclubs and long-term care facilities can become dangerous incubators of diseases. With regards to healthcare facilities the risk is exponentially higher, as many of the patients are in a weakened condition due to illness. In many cases, a microorganism that would not be a major threat to an overall healthy person can be fatal to someone with a compromised immune system or simply very elderly. Potentially dangerous microorganisms are deposited in health care facilities and elsewhere by a variety of means and tend to settle on many commonly contacted surfaces, including wheelchairs, ramps, door handles, food trays, washrooms, desks etc. Effective and thorough cleaning, sanitization and disinfection of all types of hard surfaces, such as the previously mentioned items, with appropriate compositions assists in slowing the growth or substantially containing the spread risks of such microorganisms.

Quaternary ammonium-based liquid hard surface cleaners are commonly used, typically as bathroom cleaners. Certain quaternary ammonium compounds can be effective antimicrobial agents in small dosages in these cleaners. However, quaternary ammonium compounds are lung irritants and can contribute to asthma and other breathing problems. They are also known as skin irritants, where their use may lead to unsightly rashes. Some recent data seems to indicate that exposure to quaternary ammonium compounds harms sperm quality, reduces fertility and results in birth defects in mice. Moreover, as the presence of the quaternary ammonium compounds lingers on surfaces treated with such cleaning compounds for long periods of time, it is thought that this is a factor in the emergence of viruses which are resistant to these compounds. Since such compounds linger for a period of time after application, even after wiping off, it is not recommended to use these types of compounds in and around food preparation areas or food handling areas, schools or health care facilities. Hence, both residential and commercial kitchens as well as food processing plants should avoid the presence and use of quaternary ammonium compounds. It is common to cycle quat based systems so as not to allow of resistance by germs to be gained, although many facilities do not adhere to this practice. It would be beneficial to utilized sanitization chemistry that does not promote such resistance by common germs and that has no major negative side effects such as those listed above.

Baker et al., U.S. Pat. No. 4,690,779, demonstrated a hard surface cleaner having improved non-streaking/filming properties in which a combination of low molecular weight polymer (e.g., polyethylene glycol) and certain surfactants were combined.

Corn et al., E.P. 0393772 and E.P. 0428816, describe hard surface cleaners containing anionic surfactants with ammonium counterions, and additional adjuncts.

G.B. 2,160,887 describes a cleaning system in which a combination of nonionic and anionic surfactants (including an alkanolamine salt alkyl sulfate) is contended to enhance cleaning efficacy.

U.S. Pat. Nos. 5,252,245, 5,437,807, 5,468,423, and 5,585,342, disclose improved glass and surface cleaners which combine either amphoteric or nonionic surfactants with solvents and effective buffers to provide excellent streaking/filming characteristics on glass and other smooth, glossy surfaces but which lack the presence of bactericides, such as quaternary ammonium compounds.

In food processing and handling there are several types of microbes, bacteria or other microorganisms with which food may come into contact. Much research has been done on such bacteria and the following provides a lower pH limit which still allows for microbial growth for the specific type of bacteria: *Clostridium perfringens* (min. pH for growth: 5.5-5.8); *Vibrio vulnificus* (min. pH for growth: 5); *Bacillus cereus* (min. pH for growth: 4.9); *Campylobacter* spp. (min. pH for growth: 4.9); *Shigella* spp. (min. pH for growth: 4.9); *Vibrio parahaemolyticus* (min. pH for growth: 4.8); *Clostridium botulinum* toxin (min. pH for growth: 4.6); *Clostridium botulinum* growth (min. pH for growth: 4.6); *Staphylococcus aureus* growth (min. pH for growth: 4); *Staphylococcus aureus* toxin (min. pH for growth: 4.5); Enterohemorrhagic *Escherichia coli* (min. pH for growth: 4.4); *Listeria monocytogenes* (min. pH for growth: 4.39); *Salmonella* spp (min. pH for growth: 4.21); and *Yersinia enterocolitica* (min. pH for growth: 4.2).

Mildly acidic cleaners are used to dissolve hard water deposits, remove mild rust stains, and eliminate soap film from common washroom and cooking/cleaning areas. They are useful in removing tarnish from brass and copper. Vinegar (acetic acid) and lemon juice (citric acid) are two of the most common mild acids found in cleaning compositions. Compositions made from those weak acids are generally safe for human and animal exposure. Other, harsher acids are also often found in common household cleaning products. Commercially common acids such as vinegar remove hard water deposits from glassware, rust stains from sinks, and tarnish from brass and copper. Citric acid is a natural substance found in lemons, limes, oranges, and grapefruits. It is nontoxic, antibacterial, and antiseptic. In general, its applications mirror those of vinegar. Some commercial products containing citric acid are water-based and may cause corrosion or rust on metals. It is therefore preferably to wash and dry the metal after cleaning to prevent the formation of rust. Phosphoric acid is mild, but more acidic than vinegar or lemon juice. Generally employed for rust removal, it is generally restricted to bathroom cleaners. Commercial products employing phosphoric acid include: tub, tile, sink, and toilet bowl cleaners.

Generally, strong acidic cleaners are considered toxic. They may as well be corrosive to the surfaces on which they are applied, meaning they can dissolve metal surfaces or damage human tissue (such as eyes and skin). Their use requires personal protective equipment (gloves, safety glasses, etc.) and careful application to avoid damaging materials other than those which require cleaning. Common acids that are considered strong acids are hydrochloric acid and sulfuric acid. Hydrochloric acid is found in some toilet bowl cleaners to remove scale deposition and general grime. It is highly corrosive to metals and dermal tissue. In commercial products, hydrochloric acid can be utilized to clean or etch concrete by consuming the top layer of concrete and or creating a porous surface for optimal coating or paint adhesion. Sulfuric acid is also utilized as an effective drain cleaner and can also be found in some toilet bowl cleaners. It is also considered a powerful oxidizer. These common mineral acids are now beginning to be banned for sale to the public in some jurisdictions, such as Europe, where they are utilized as a weapon by throwing in peoples faces or in some cases as components utilized in chemical weapons or explosives.

Another acid which may be mistakenly considered a strong mineral acid is hydrofluoric acid (used as a commercial rust remover, glass etch or aluminum polisher) has many negatives such as it will cause severe dermal burns, is highly toxic, is easily absorbed through the skin and fatal in some cases of even small exposure events. One must also take care to avoid exposing glass windows or glass products, which will be etched or dissolved. Oxalic acid is a bleaching agent used to remove rust. It is, however, quite toxic if it is inhaled or swallowed, and corrosive. It can also be unknowingly ingested indirectly if the surfaces cleaned (i.e., utensils, bowls, plates, etc.) come into contact with food destined for consumption.

Other compounds such as sodium bisulfate (found in some toilet bowl cleaners) is a poison and requires extreme caution; and sodium hypochlorite (found in some in bleaching solutions, disinfectants, water purifiers, and cleaning products). Sodium hypochlorite when used as a disinfectant destroys bacteria, viruses, and mold. Breathing or ingesting this compound may cause poisoning.

In light of the prior art and limits for microbial growth for a number of extremely problematic bacteria, the inventors have devised a novel approach for the cleaning of hard surfaces all the while minimizing the use of chemicals such as quaternary amines and bleach, both of which are very harmful for long term human exposure.

Hydrogen peroxide has been used as an antiseptic since the 1920s because it kills bacteria cells by destroying their cell walls. It does so through the process of oxidation. Unfortunately, peroxides as a group are not stable molecules.

In order to clean surfaces from the possible presence of viruses, the U.S. Centers for Disease Control and Prevention (the CDC) recommends first cleaning surfaces with soap and water, and then disinfecting them with EPA-registered household disinfectants which include: diluted bleach (the CDC recommends one part bleach to 50 parts water, while the Public Health Agency of Canada recommends one part bleach to nine parts water); and solutions containing at least 70 percent alcohol. The two-step approach may work for some, but can also cause problems for others and is much more difficult to apply in an industrial (manufacturing, food processing, dairy's, breweries, warehouses or abattoirs for example) setting.

In light of the above, there still exists a need for an improved composition for cleaning and sanitizing hard surfaces which is cost effective and carries little or no future impact on the environment and/or on the possibility of microorganism adaptation or immunity. The present invention addresses the drawbacks of the prior art by providing an effective surface cleaning composition which combines a low pH with an oxidizing agent to ensure a substantially complete destruction of bacteria on a hard surface without resorting to alcohol-based solution.

SUMMARY OF THE INVENTION

According to an aspect of the present invention, there is provided an aqueous, antimicrobial hard surface cleaning composition, said composition comprising:
an arylsulfonic acid;
a source of peroxide;
an effective amount of a stabilizer; and
water.

According to an object of the present invention, there is provided a method to improve microorganism contaminant removal from hard surfaces. According to a preferred embodiment, the microorganism contaminant being removed is selected from the group consisting of viruses, bacteria, fungi and microbes.

According to a preferred embodiment of the present invention, there is provided an aqueous, antimicrobial hard surface cleaning composition, said composition consisting of an arylsulfonic acid; a source of peroxide; an effective amount of a stabilizer; and water.

According to a preferred embodiment of the present invention, there is disclosed a method of cleaning and disinfecting a hard surface by applying a preferred composition to a contaminated surface and removing both from said surface.

Accordingly, there is a need, both in industry and in the home, for a safe and effective microbiocidal cleaner, sanitizer and/or disinfectant that can be used on a wide variety of surfaces.

According to a preferred embodiment of the present invention, there is provided a microbiocidal cleanser or disinfectant that will kill or inhibit a wide variety of microorganisms.

According to a preferred embodiment of the present invention, there is provided a microbiocidal cleaner, sanitizer and/or disinfectant that is safe for use around humans and animals.

It is an object of the present invention to provide a hard surface cleaner which does not exhibit long term latency as is found with quaternary ammonium compounds.

According to an object of the present invention, there is provided a composition for use as a hard surface cleaner, disinfectant and/or sanitizer, said composition comprising:
an arylsulfonic acid;
a source of peroxide;
an effective amount of a stabilizer; and
water.

Preferably, the arylsulfonic acid is present in an amount ranging from 0.5 to 5 w/w % of the total weight of the composition.

According to a preferred embodiment of the present invention, there is provided a composition for use as a hard surface cleaner, disinfectant and/or sanitizer, said composition consisting of: an arylsulfonic acid; a source of peroxide; an effective amount of a stabilizer; and water.

Preferably, said source of peroxide is present in an amount ranging from 0.5 to 10 w/w % of the total weight of the composition. More preferably, said source of peroxide is present in an amount ranging from 0.5 to 7.5 w/w % of the total weight of the composition. Even more preferably, said source of peroxide is present in an amount ranging from 0.5 to 5 w/w % of the total weight of the composition.

Preferably also, said stabilizer is present in an amount ranging from 0.05 to 5 w/w % of the total weight of the composition. More preferably, said stabilizer is present in an amount ranging from 0.05 to 3 w/w % of the total weight of the composition. Even more preferably, said stabilizer is present in an amount ranging from 0.05 to 2 w/w % of the total weight of the composition. According to a preferred embodiment of the present invention, the stabilizer is present in an amount ranging from 0.05 to 1 w/w % of the total weight of the composition.

Preferably, said arylsulfonic acid is selected from the group consisting of: arylalkylsulfonic acids where the alkyl groups range from $C_1$-$C_6$ and are linear or branched; and combinations thereof. Preferably, said arylsulfonic or arylalkylsulfonic acid is selected from the group consisting of: benzenesulfonic acid, toluene sulfonic acid, monoalkylbenzene sulfonic acid, where R1 is $C_2$ to $C_6$, dialkylbezene sulfonic acid, where $R_1$ is $C_1$ to $C_6$ and $R_2$ is $C_1$ to $C_6$; and combinations thereof.

More preferably, said arylalkylsulfonic acid is toluenesulfonic acid. Also preferably, said arylalkylsulfonic acid has a molecular weight below 300 g/mol. Also preferably, said arylsulfonic acid has a molecular weight below 175 g/mol.

According to a preferred embodiment of the present invention, the source of peroxide is selected from the group consisting of: hydrogen peroxide; benzoyl peroxide; percarbonates; perborates; persulfates; and combinations thereof. Preferably, the peroxide is hydrogen peroxide.

According to a preferred embodiment of the present invention, the stabilizer is an alkanolamine. Preferably, the alkanolamine is selected from the group consisting of: monoethanolamine; diethanolamine; triethanolamine; and combinations thereof. More preferably, the alkanolamine is monoethanolamine. According to another preferred embodiment of the present invention, the alkanolamine is diethanolamine. According to yet another preferred embodiment of the present invention, the alkanolamine is triethanolamine.

According to a preferred embodiment of the present invention, the stabilizer is selected from the group consisting of: taurine; taurine derivatives; and taurine-related compounds. Preferably also, said taurine derivative or taurine-related compound is selected from the group consisting of: sulfamic acid; taurolidine; taurocholic acid; tauroselcholic acid; tauromustine; 5-taurinomethyluridine and 5-taurinomethyl-2-thiouridine; homotaurine (tramiprosate); acamprosate; and taurates; as well as aminoalkylsulfonic acids where the alkyl is selected from the group consisting of $C_1$-$C_5$ linear alkyl and $C_1$-$C_5$ branched alkyl. Preferably, the linear alkylaminosulfonic acid is selected form the group consisting of: methyl; ethyl (taurine); propyl; and butyl. Preferably, the branched aminoalkylsulfonic acid is selected from the group consisting of: isopropyl; isobutyl; and isopentyl.

According to a preferred embodiment of the present invention, the stabilizer is selected from the group consisting of: sulfanilic acid; orthanilic acid; and metanilic acid.

According to a preferred embodiment of the present invention, the composition has a pH of less than 3. Preferably, the composition has a pH of less than 2. Even more preferably, the composition has a pH of less than 1.5, more preferably, the pH is close to 1. Even more preferably, the composition has a pH of less than 1.0. In that respect, in some instances, the pH can reach close to 0.5.

According to an object of the present invention, there is provided a method of cleaning a hard surface, wherein said method comprises the steps of:
providing a composition according to the above;
providing a surface which requires cleaning; and
applying the composition onto said surface for a duration of time sufficiently long enough to destroy microorganisms present on said surface.

According to another object of the present invention, there is provided a method of disinfecting a hard surface, wherein said method comprises the steps of:
providing a composition according to the above;
providing a surface which requires disinfecting; and
applying the composition onto said surface for a duration of time sufficiently long enough to destroy microorganisms present on said surface.

According to yet another object of the present invention, there is provided a method of sanitizing a hard surface, wherein said method comprises the steps of:
providing a composition according to the above;
providing a surface which requires sanitizing; and
applying the composition onto said surface for a duration of time sufficiently long enough to destroy microorganisms present on said surface.

DETAILED DESCRIPTION OF THE INVENTION

The present invention is an aqueous acidic composition for cleaning, sanitizing, and/or disinfecting hard surfaces.

According to a preferred embodiment of the present invention, the composition is a multi-purpose aqueous acid hard surface cleaner, sanitizer, and/or disinfectant. Preferably, these types of cleaners are intended to clean hard surfaces by application of a metered discrete amount of the cleaner, typically by pump or trigger sprayer onto the surface to be cleaned or onto the workpiece, such as a soft cloth or sponge, and then wiping the surface, thus removing contaminants present. According to another preferred embodiment, the composition may be applied by pouring a predetermined amount onto a surface and subsequently removing such with a cloth or the like.

According to an aspect of the present invention, there is provided a composition for cleaning a hard surface comprised of:
 an arylsulfonic acid;
 a source of peroxide;
 an effective amount of a stabilizer; and
 water.

According to a preferred embodiment of the present invention, the arylsulfonic acid is present in an amount ranging from 0.5 to 5 w/w % of the total weight of the composition.

According to a preferred embodiment of the present invention, the source of peroxide is present in an amount ranging from 0.5 to 5 w/w % of the total weight of the composition.

According to a preferred embodiment of the present invention, the stabilizer is present in an amount ranging from 0.05 to 1 w/w % of the total weight of the composition.

According to a preferred embodiment of the present invention, when used for example, in agricultural applications, the content of arylsulfonic acid and the source of peroxide can have a concentration of up to 20 w/w %. Some farm installations on farms may require, at some point in time, the application of a composition capable of cleaning, disinfecting and or sanitizing large surfaces contaminated with high quantities of microbes or other toxins. In those instances, it may be preferable to use a composition of arylsulfonic acid and peroxide of 10 w/w/% or even up to 20 w/w %. Large surfaces treated are typically sprayed with the composition and allowed to drip and drain into a large drain which, if left untreated, may be directed to an external environment with no further treatment. In such cases, it is highly desirable to have a composition which is readily biodegradable. That is to say, the arylsulfonic acid and the stabilizers are biodegradable. Therefore, if or when those components migrate into the environment, those will be biodegradable.

Preferably the arylsulfonic acid is selected from the group consisting of: arylalkylsulfonic acids where the alkyl groups range from $C_1$-$C_6$ and are linear or branched; and combinations thereof. Preferably, said arylsulfonic or arylalkylsulfonic acid is selected from the group consisting of: benzenesulfonic acid, toluene sulfonic acid, monoalkylbenzene sulfonic acid, where R1 is C2 to C6, dialkylbezene sulfonic acid, where $R_1$ is $C_1$ to $C_6$ and $R_2$ is $C_1$ to $C_6$; and combinations thereof.

According to a preferred embodiment of the present invention, the compound comprising a sulfonic acid moiety is toluenesulfonic acid (TSA). TSA is a desirable acid to use as it is virtually non-fuming and biodegradable. Hence, once the acid composition has been used it can be rinsed and disposed of in the environment and will not cause any unwanted effects. Moreover, TSA can be used on several types of metallic surfaces including stainless steel on which many food processing operations are carried out without corroding or rusting the surface.

Preferably, the source of peroxide is selected from the group consisting of: hydrogen peroxide; benzoyl peroxide; percarbonates; perborates; persulfates; and combinations thereof. Preferably, the source of peroxide is hydrogen peroxide. Preferably, any cheap source of peroxide should be considered.

According to a preferred embodiment of the present invention, the stabilizer is an alkanolamine.

According to a preferred embodiment of the present invention, the stabilizer is selected from the group consisting of: taurine; taurine derivatives; and taurine-related compounds. Preferably also, said taurine derivative or taurine-related compound is selected from the group consisting of: sulfamic acid; taurolidine; taurocholic acid; tauroselcholic acid; tauromustine; 5-taurinomethyluridine and 5-taurinomethyl-2-thiouridine; homotaurine (tramiprosate); acamprosate; and taurates; as well as aminoalkylsulfonic acids where the alkyl is selected from the group consisting of $C_1$-$C_5$ linear alkyl and $C_1$-$C_5$ branched alkyl. Preferably, the linear alkylaminosulfonic acid is selected form the group consisting of: methyl; ethyl (taurine); propyl; and butyl. Preferably, the branched aminoalkylsulfonic acid is selected from the group consisting of: isopropyl; isobutyl; and isopentyl.

According to a preferred embodiment of the present invention, the alkanolamine is selected from the group consisting of: monoethanolamine; diethanolamine; triethanolamine; and combinations thereof. Preferably, the alkanolamine is monoethanolamine.

According to another preferred embodiment of the present invention, the alkanolamine is diethanolamine.

According to yet another preferred embodiment of the present invention, the alkanolamine is triethanolamine.

According to a preferred embodiment of the present invention, the composition has a pH of less than 3. Preferably, the composition has a pH of less than 2.

According to another preferred embodiment of the present invention, the composition has a pH of less than 1.

According to another aspect of the present invention, there is provided a method of cleaning a hard surface, wherein said method comprises the steps of:
 providing a composition according to the above;
 providing a surface which requires cleaning; and
 applying the composition onto said surface for a duration of time sufficiently long enough to destroy microorganisms present on said surface.

Preferably, additional additives such as fragrance, dye and the like can be included to provide desirable attributes to the composition.

In the present description, effective amounts are generally those amounts listed as the ranges or levels of ingredients in the descriptions which follow hereto. Unless otherwise stated, amounts listed in percentage ("%'s") are in weight percent of the composition.

Water

According to a preferred embodiment of the present invention, the composition is mainly comprised of water with relatively low levels of active ingredients such as acid and peroxide.

According to a preferred embodiment deionized water is used. According to another preferred embodiment tap water is used. Preferably, the type of water can be selected from the group consisting of: reverse osmosis; deionized; distilled and tap water.

According to a preferred embodiment of the present invention, the composition further comprises at least one surfactant. Preferably, the surfactant can be selected from the group consisting of anionic; cationic; non-ionic; and amphoteric surfactants. Preferably, the amphoteric surfactant is selected from the group consisting of a sultaine surfactant; a betaine surfactant; and combinations thereof. More preferably, the sultaine surfactant and betaine surfactant are selected from the group consisting of an amido betaine surfactant; an amido sultaine surfactant; and combinations thereof. Yet even more preferably, the amido betaine surfactant and is selected from the group consisting of an amido betaine comprising a hydrophobic tail from $C_8$ to $C_{16}$. Most preferably, the amido betaine comprising a hydrophobic tail from $C_8$ to $C_{16}$ is cocamidobetaine.

Preferably also, the composition further comprises an anionic surfactant. Preferably, the anionic surfactant is a carboxylic surfactant. More preferably, the carboxylic surfactant is a dicarboxylic surfactant. Even more preferably, the dicarboxylic surfactant comprises ahydrophobic tail ranging from C8 to C16. Most preferably, the dicarboxylic surfactant is sodium lauriminodipropionate.

A preferred embodiment can refer to a composition comprising cocamidopropyl betaine and β-Alanine, N-(2-carboxyethyl)-N-dodecyl-, sodium salt (1:1).

According to a preferred embodiment of the present invention, the composition further comprises an amine oxide surfactant. Such surfactants are desirable as they have good foaming properties and can help in the removal of solid contaminants when cleaning; disinfecting; and/or sanitizing hard surfaces.

According to a preferred embodiment of the present invention, a small amount of additives can be incorporated for improving the cleaning performance or aesthetic qualities of the cleaner. Adjuncts for cleaning include additional surfactants, such as those described in Kirk-Othmer, Encyclopedia of Chemical Technology 3rd Ed., Volume 22, pp. 332-432 (Marcel-Dekker, 1983), which are incorporated herein by reference. Aesthetic adjuncts include fragrances, such as those available from Givaudan, IFF, Quest and others, and dyes and pigments which can be solubilized or suspended in the formulation, such as diaminoanthraquinones. The amount of these cleaning and aesthetic additives should remain low and should preferably not consist of more than 1% by weight of the total weight of the composition.

Example 1

According to a preferred embodiment of the present invention, a composition was prepared by admixing water, toluenesulfonic acid and hydrogen peroxide to yield a concentration of each component as follows:
Toluenesulfonic acid—1.25 w/w %
Hydrogen peroxide—1.00 w/w %
Stabilizer—0.10 w/w %
Water—98.2 w/w %

The pH of the resulting composition was between 1.2 and 1.4. The stabilizer selected for Example 1 was monoethanolamine.

Example 2

According to a preferred embodiment of the present invention, a composition was prepared by admixing water, toluenesulfonic acid and hydrogen peroxide to yield a concentration of each component as follows:
Toluenesulfonic acid—3.00 w/w %
Hydrogen peroxide—2.50 w/w %
Stabilizer—0.25 w/w %
Water—95.55 w/w %

The pH of the resulting composition was below 1. The stabilizer selected for Example 1 was monoethanolamine.

Example 3

According to a preferred embodiment of the present invention, a composition was prepared by admixing water, toluenesulfonic acid and hydrogen peroxide to yield a concentration of each component as follows:

Toluenesulfonic acid—5.00 w/w %
Hydrogen peroxide—5.00 w/w %
Stabilizer—0.50 w/w %
Water—91.0 w/w %

The pH of the resulting composition was approximately 0.5. The stabilizer selected for Example 1 was monoethanolamine.

US DOT Testing for Stainless Steel Compatibility

Based on prior testing with TSA exposed to stainless steel, it was assessed that such an acidic composition is compatible therewith in accordance with the United States Department of Transportation (US DOT) testing for stainless steel compatibility.

While the foregoing invention has been described in some detail for purposes of clarity and understanding, it will be appreciated by those skilled in the relevant arts, once they have been made familiar with this disclosure, that various changes in form and detail can be made without departing from the true scope of the invention in the appended claims.

The invention claimed is:

1. A composition for use as a hard surface cleaner, disinfectant and/or sanitizer, said composition comprising:
    an arylsulfonic acid;
    a source of peroxide;
    an effective amount of a stabilizer; said stabilizer selected from the group consisting of: taurine; taurolidine; taurocholic acid; tauroselcholic acid; tauromustine; 5-taurinomethyluridine; 5-taurinomethyl-2-thiouridine; homotaurine; acamprosate; and aminoalkylstilfonic acid where the alkyl of the aminoalkylsulfonic acid is selected from the group consisting of $C_1$-$C_5$ linear alkyl and $C_1$-$C_5$ branched alkyl; water; and
    wherein said composition has a pH of less than 2.

2. The composition according to claim 1, where said arylsulfonic acid is present in an amount ranging from 0.5 to 5 w/w % of the total weight of the composition.

3. The composition according to claim 1, where said source of peroxide is present in an amount ranging from 0.5 to 10 w/w % of the total weight of the composition.

4. The composition according to claim 1, where said stabilizer is present in an amount ranging from 0.05 to 5 w/w % of the total weight of the composition.

5. The composition according to claim 1, where said arylsulfonic acid is selected from the group consisting of: arylsulfonic acids and substituted arylsulfonic acids.

6. The composition according to claim 1, where said arylsulfonic acid is selected from the group consisting of: arylsulfonic acids and arylalkylsulfonic acids where the alkyl groups range from $C_1$-$C_6$ and are linear or branched; and combinations thereof.

7. The composition according to claim 6, where said arylsulfonic or arylalkylsulfonic acid is selected from the group consisting of: benzenesulfonic acid, toluene sulfonic acid, monoalkylbenzene sulfonic acid and combinations thereof.

8. The composition according to claim 1, where said aryistilfonic acid is toluenestilfonic acid.

9. The composition according to claim 1, where said arylsulfonic acid has a. molecular weight below 300 g/mol.

10. The composition according to claim 1, where said source of peroxide is selected from the group consisting of: hydrogen peroxide; benzoyl peroxide; percarbonates; perborates; persulfates; and combinations thereof.

11. The composition according to claim 1, where the peroxide is hydrogen peroxide.

12. The composition according to claim 1 where said alkyl of the alkylaminosulfonic acid is selected form the group consisting of: methyl; ethyl; propyl; and butyl.

13. The composition according to claim 1 where said alkyl of the aminoalkyisulthnic acid is selected from the group consisting of: isopropyl; isobutyl; and isopentyl.

14. The composition according to claim 1, where the stabilizer is monoethanolamine.

15. A method of cleaning, disinfecting and/or sanitizing a hard surface, wherein said method comprises the steps of:
   providing a composition according to claim 1;
   providing a surface which requires cleaning; and
   applying the composition onto said surface for a duration of time sufficiently long enough to destroy microorganisms present on said surface.

16. The composition according to claim 1, where said arylsulfonic acid has a molecular weight below 175 g/mol.

* * * * *

UNITED STATES PATENT AND TRADEMARK OFFICE
CERTIFICATE OF CORRECTION

| | |
|---|---|
| PATENT NO. | : 12,043,820 B2 |
| APPLICATION NO. | : 17/705142 |
| DATED | : July 23, 2024 |
| INVENTOR(S) | : Clay Purdy et al. |

It is certified that error appears in the above-identified patent and that said Letters Patent is hereby corrected as shown below:

In the Claims

In Claim 8, the term "aryistilfonic" should be corrected as "arylsulfonic"

In Claim 8, the term "toluenestilfonic" should be corrected as "toluenesulfonic"

In Claim 13, the term "aminoalkyisulthnic" should be corrected as "aminoalkylsulfonic"

Signed and Sealed this
Seventeenth Day of September, 2024

Katherine Kelly Vidal
*Director of the United States Patent and Trademark Office*